United States Patent [19]
Link

[11] Patent Number: 4,564,020
[45] Date of Patent: Jan. 14, 1986

[54] METHOD AND APPARATUS FOR OBTAINING AN INDIVIDUAL'S SYSTOLIC BLOOD PRESSURE

[75] Inventor: William T. Link, Berkeley, Calif.

[73] Assignee: Norse Instruments, Inc., Hayward, Calif.

[21] Appl. No.: 622,079

[22] Filed: Jun. 19, 1984

[51] Int. Cl.⁴ .............................................. A61B 5/02
[52] U.S. Cl. ..................................... 128/677; 128/688
[58] Field of Search ....................... 128/677, 680–683, 128/687–688, 672

[56] References Cited

U.S. PATENT DOCUMENTS

| | | | |
|---|---|---|---|
| 3,903,872 | 9/1975 | Link | 128/681 |
| 4,009,709 | 3/1977 | Link et al. | 128/681 |
| 4,074,711 | 2/1978 | Link et al. | 128/681 |
| 4,137,907 | 2/1979 | Jansen et al. | 128/681 |
| 4,140,110 | 2/1979 | Jansen et al. | 128/681 |
| 4,154,238 | 5/1979 | Link | 128/681 |
| 4,174,707 | 11/1979 | Link et al. | 128/681 |
| 4,177,801 | 12/1979 | Grangirard et al. | 128/681 |
| 4,367,751 | 1/1983 | Link et al. | 128/681 X |
| 4,484,584 | 11/1984 | Vemura | 128/680 |

Primary Examiner—Lee S. Cohen
Assistant Examiner—Angela D. Sykes
Attorney, Agent, or Firm—Flehr, Hohbach, Test, Albritton & Herbert

[57] ABSTRACT

A specific technique for determining an individual's systolic blood pressure is disclosed herein. This technique utilizes the individual's diastolic blood pressure, the patient's arterial curve or amplitude curve, and different assumed systolic pressures for making a comparison between certain assumed curves and a reference curve in order to establish which of the assumed systolic pressures accurately reflects the individual's actual systolic pressure.

8 Claims, 9 Drawing Figures

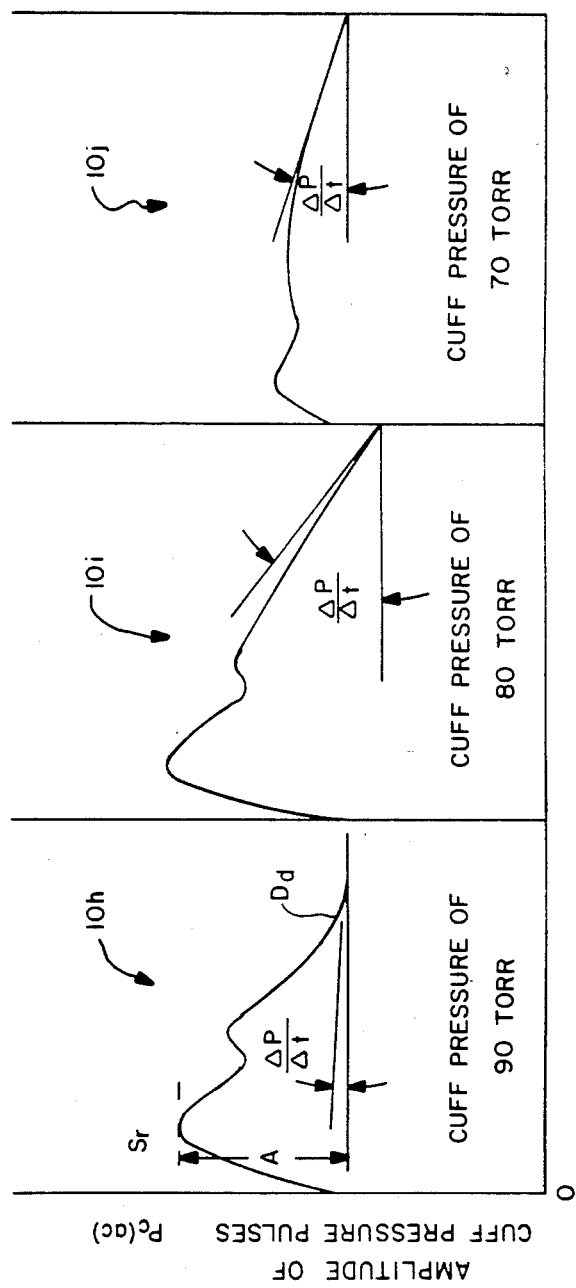
FIG.—1

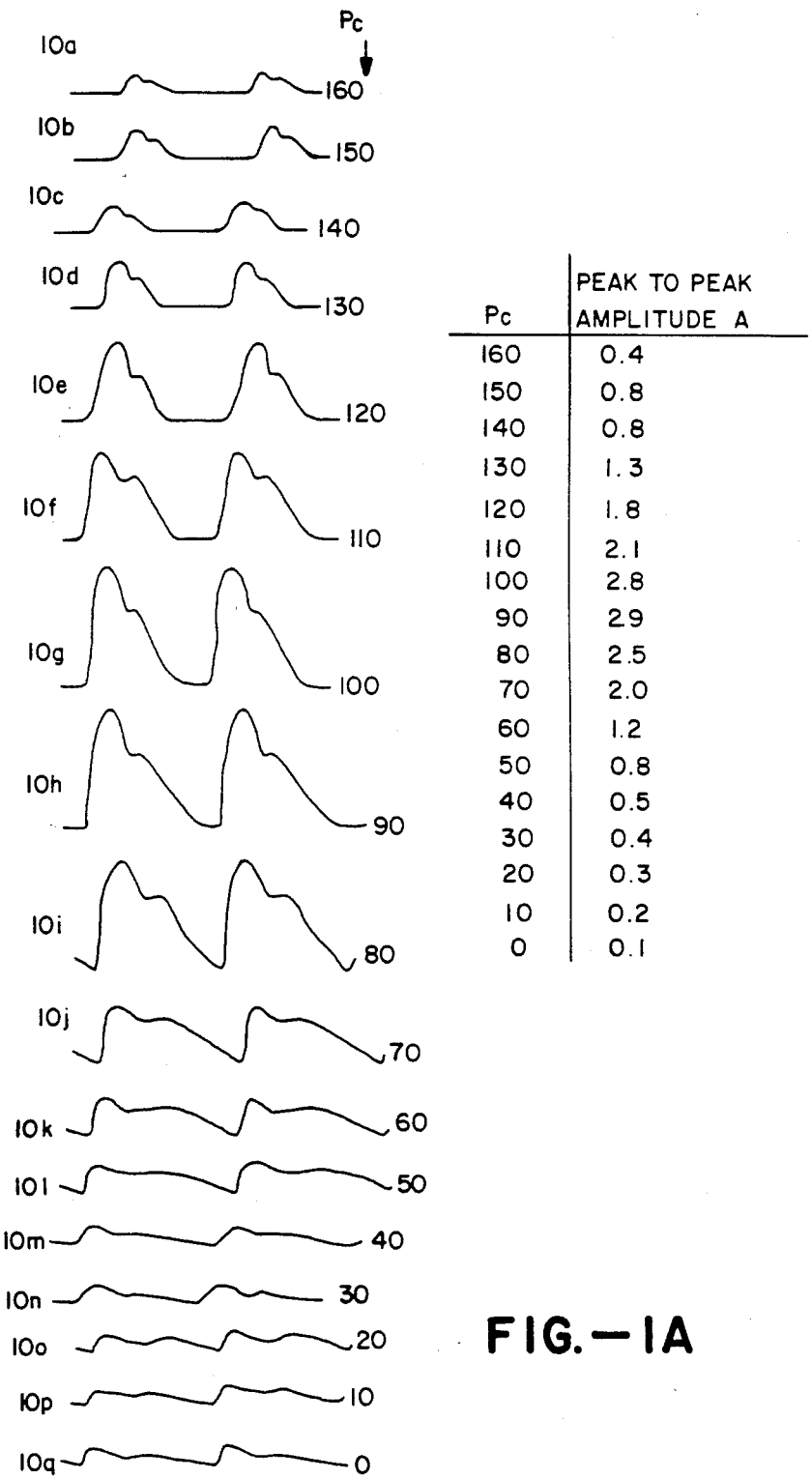
FIG.—1A

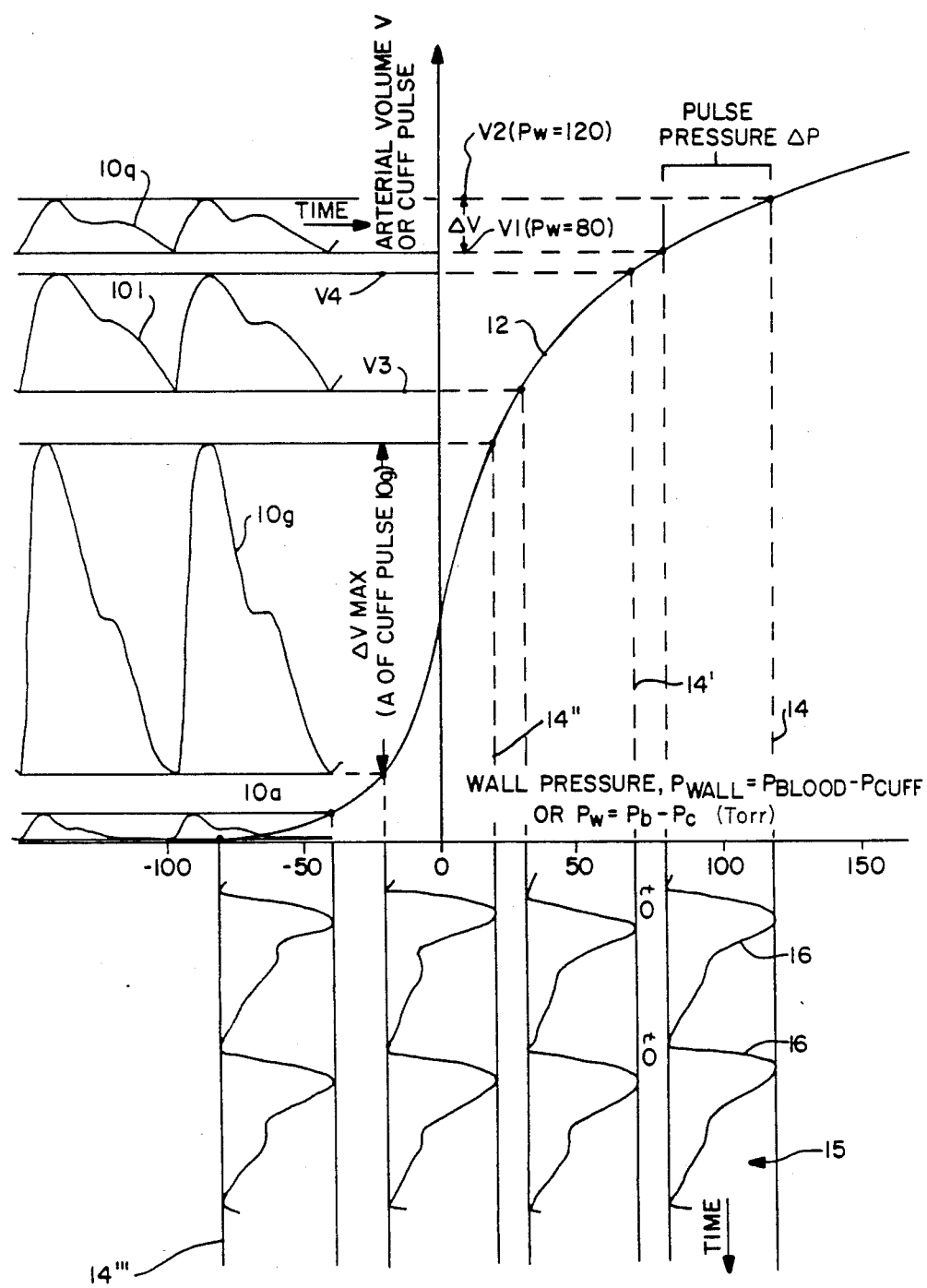
FIG.—2

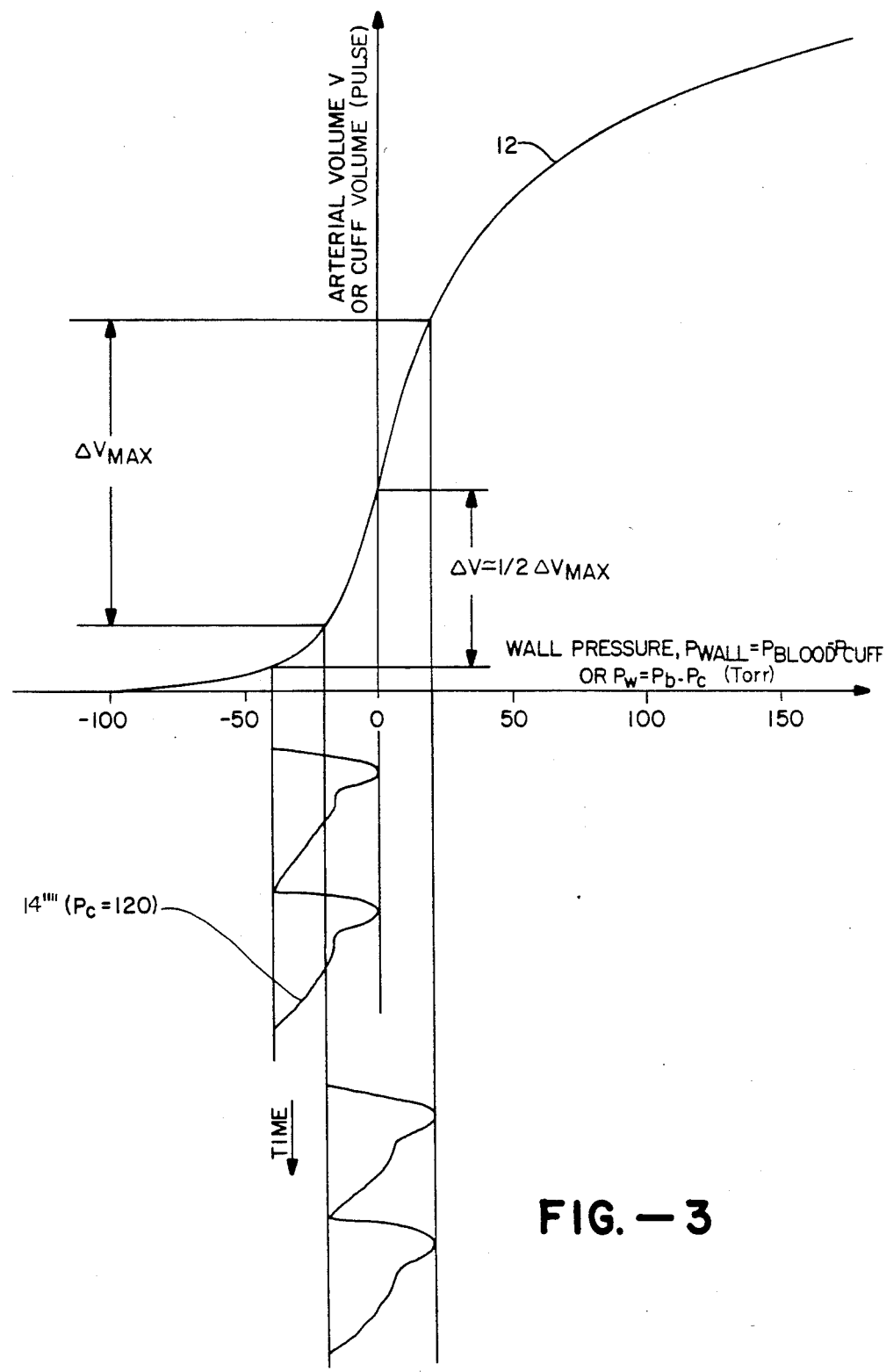
FIG.—3

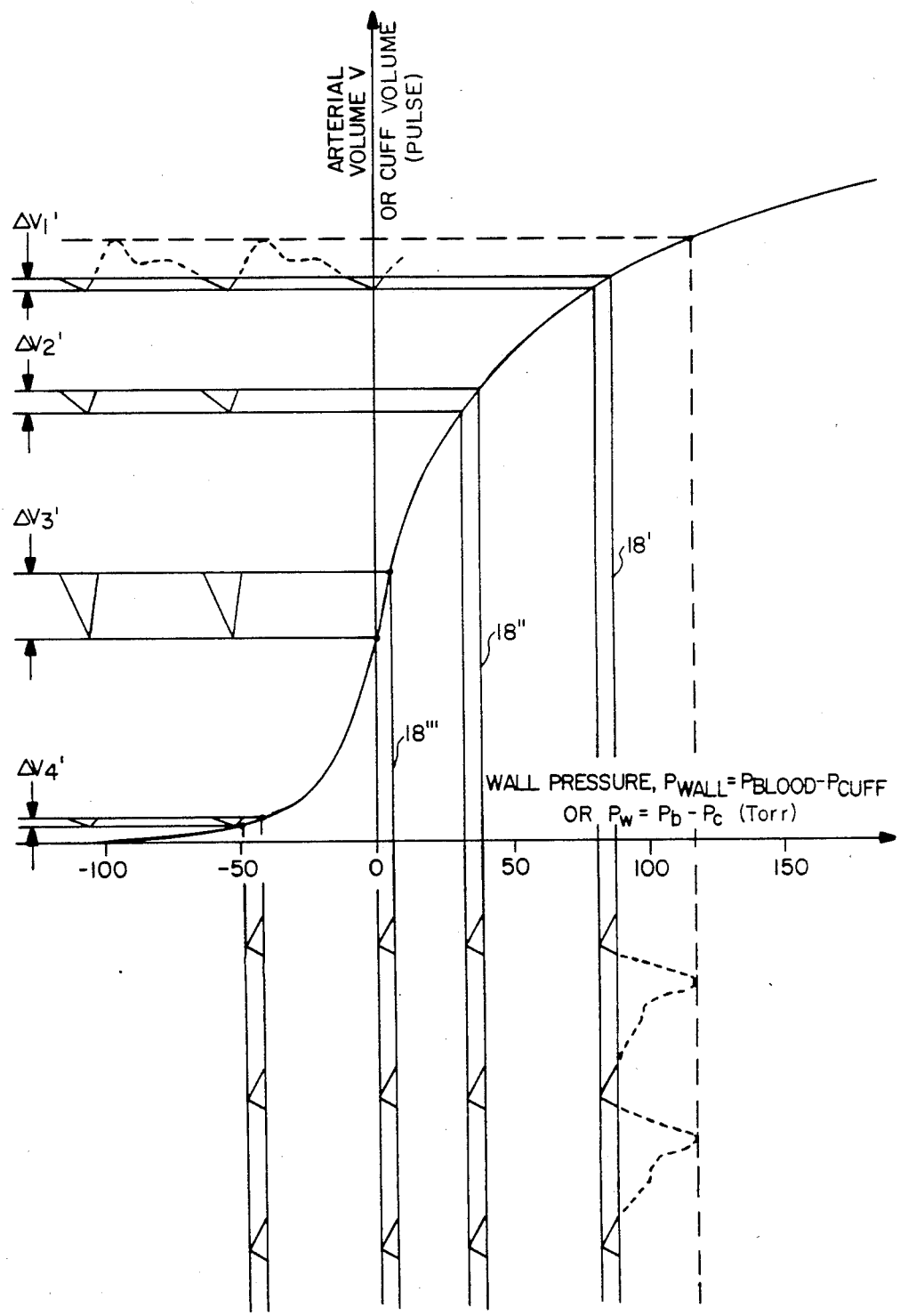
FIG.—4

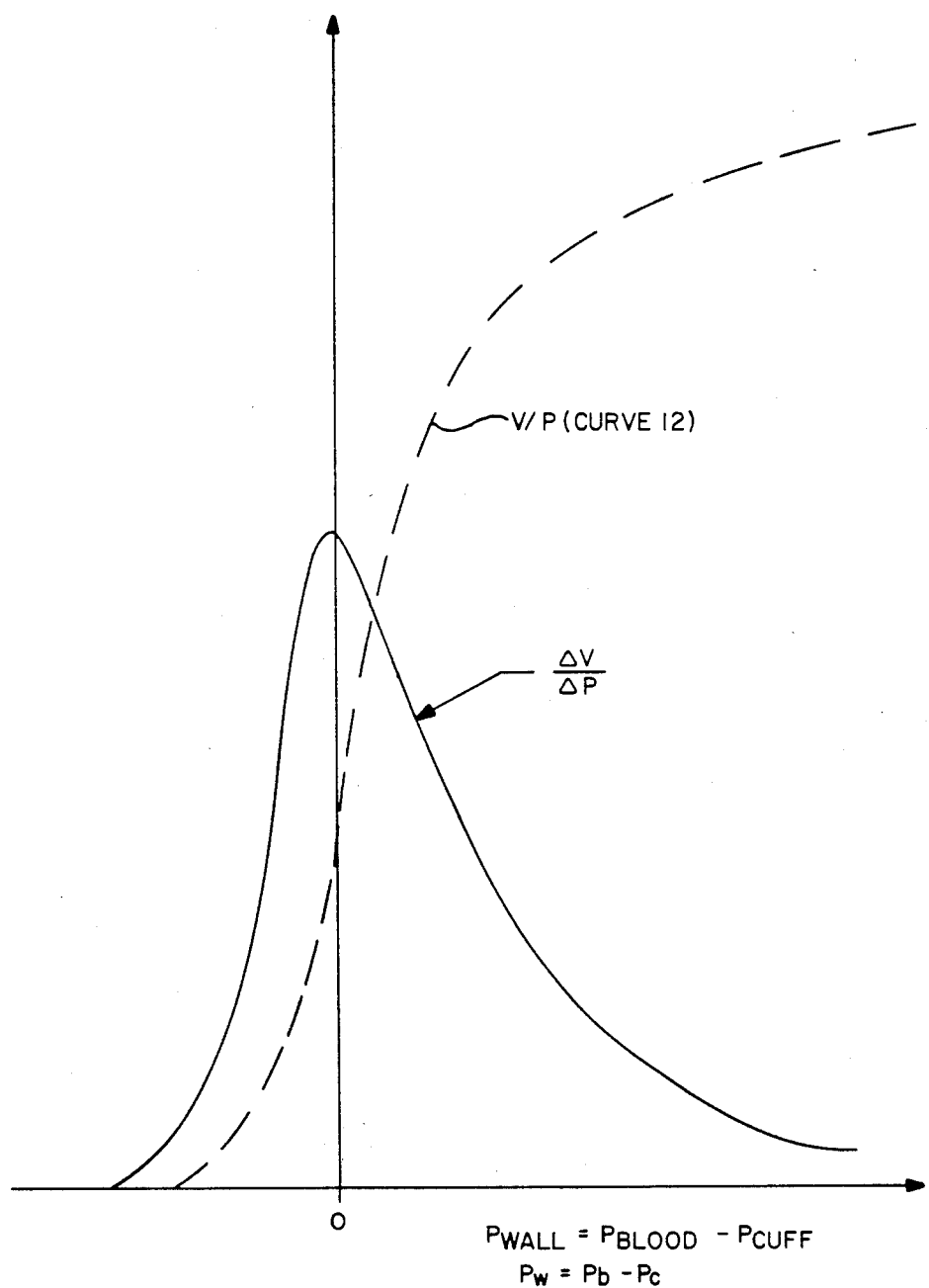
FIG. — 5

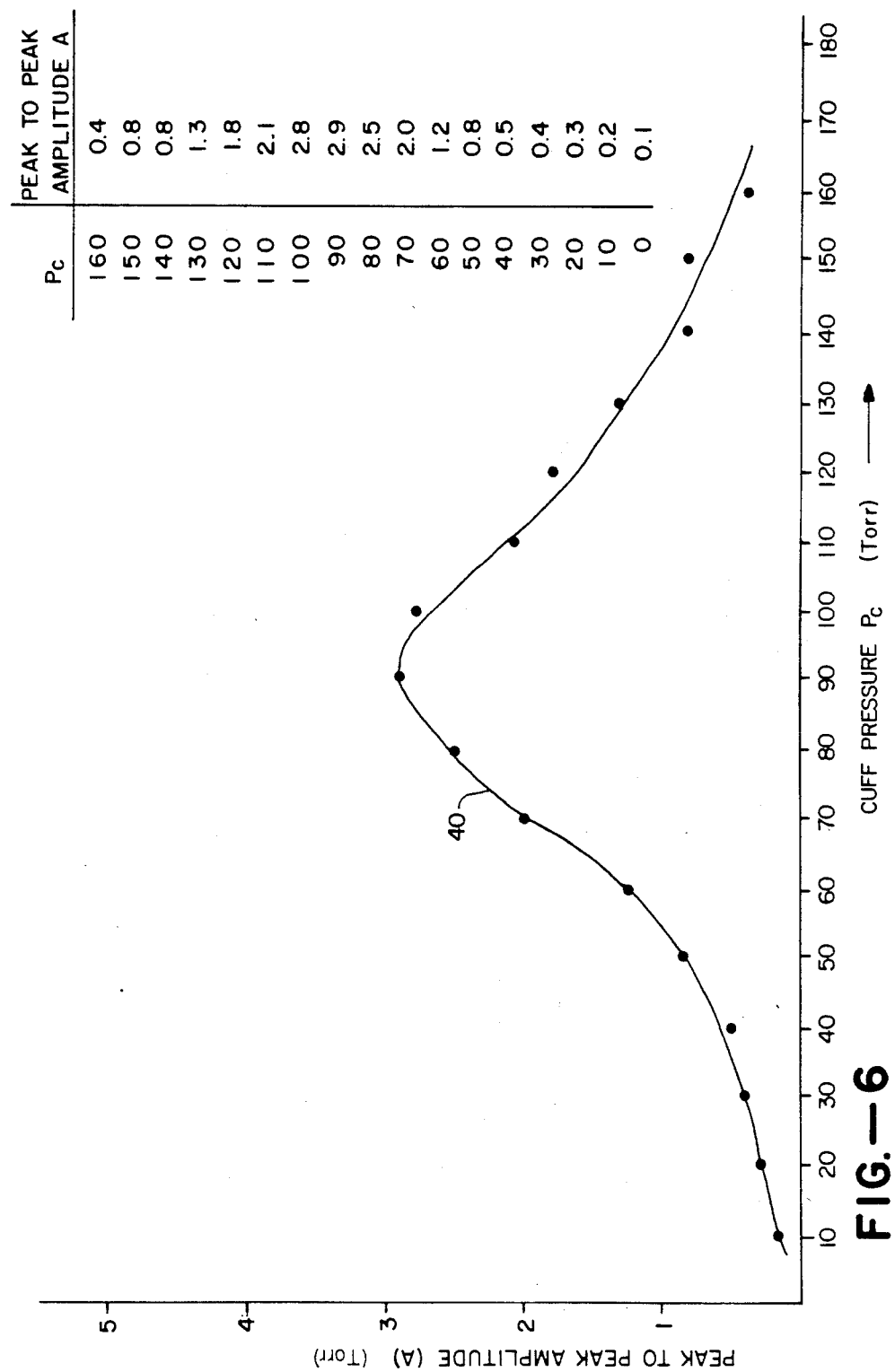
FIG.—6

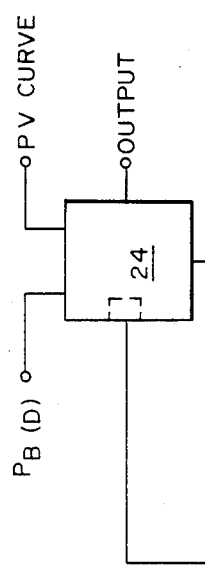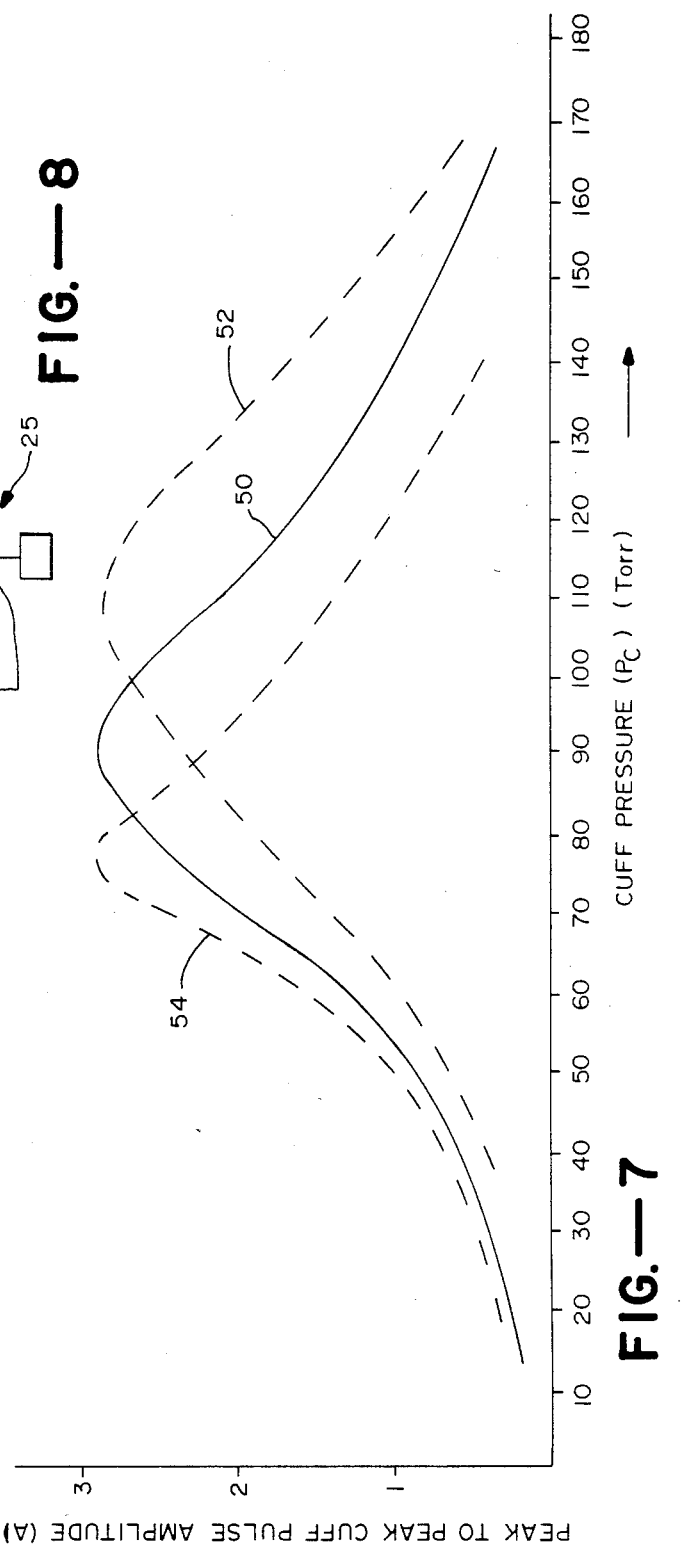

METHOD AND APPARATUS FOR OBTAINING AN INDIVIDUAL'S SYSTOLIC BLOOD PRESSURE

BACKGROUND OF THE INVENTION

The present invention relates generally to blood pressure evaluation procedures and more particularly to a specific non-invasive technique for determining the systolic blood pressure of a given individual.

The most reliable ways presently known for obtaining information relating to an individual's blood pressure require invasive procedures. Such procedures are not carried out routinely but only under extreme circumstances, for example during heart surgery. Under less critical conditions, blood pressure information including specifically an individual's systolic (maximum) and diastolic (minimum) blood pressures is obtained non-invasively. There are two well known non-invasive techniques presently being used today, one is commonly referred to as auscultation and the other is based on oscillometry. Both of these non-invasive techniques use the standard arm cuff which most people are familiar with. However, in the auscultatory method, the systolic and diastolic pressures are determined by listening to certain sounds (Korotkoff sounds) which occur as a result of the cuff first being pressurized and then depressurized whereas oscillometry actually measures changes in pressure in the cuff as a result of changes in blood pressure as the cuff is first pressurized and then depressurized.

As will be seen hereinafter, the various embodiments of the present invention are based on oscillometry. In order to more fully appreciate these embodiments, reference is made to applicant's own U.S. Pat. No. 3,903,872 (the Link patent) for obtaining blood pressure information non-invasively. This patent which is incorporated herein by reference describes, among other things, a way of obtaining the diastolic pressure of an individual in accordance with a technique which will be discussed in more detail hereinafter. In U.S. Pat. Nos. 4,009,709 and 4,074,711 (Link et al) which are also incorporated herein by reference, non-invasive techniques using oscillometry are disclosed for obtaining the systolic pressure of an individual. These techniques will also be discussed hereinafter.

While the various procedures described in the Link and Link et al patents just recited and other patents held by applicant are satisfactory for their intended purposes, it is an object of the present invention to provide additional uncomplicated and yet reliable techniques for obtaining different types of information relating to an individual's blood pressure.

SUMMARY OF THE INVENTION

A more specific object of the present invention is to provide an uncomplicated and yet reliable technique for determining the systolic pressure of an individual and specifically a technique which is different than those described in the previously recited Link et al U.S. Pat. Nos. 4,009,709 and 4,074,711.

As will be described in more detail hereinafter, the objects just recited are achieved by means of oscillometry. In accordance with this technique, a suitably sized cuff, for example one which is 20 inches long and 5 inches wide, is positioned around the upper arm of an individual, a human being specifically or a mammal in general (hereinafter referred to as the patient) and initially pressurized to a level which is believed to be clearly greater than the patient's systolic pressure, for example 180 Torr. It is assumed that this pressure will also cause the patient's artery within the sleeve to completely collapse. Thereafter, cuff pressure is gradually reduced toward zero during which time the cuff continuously changes in pressure in an oscillating fashion due to the combination of (1) the internal blood pressure changes in the patient's artery and (2) changes in cuff pressure. The latter at any given time in the procedure is known and oscillatory changes in cuff pressure can be readily measured, for example with an oscilloscope. By using these two parameters in conjunction with information which may be made available from methods disclosed in the above-recited United States patents it is possible to achieve the foregoing objectives in an uncomplicated and reliable way utilizing the techniques of the present invention to be described hereinafter.

In this regard, it should be noted at the outset that the typically 5" wide pressure cuff entirely surrounds a corresponding 5" length of artery. The tissue of the arm is for the most part incompressible, and therefore any change in the volume of the artery, caused for example by pulsations of blood, results in a corresponding change in the volume of air in the air bladder which is within the cuff and therefore adjacent to the arm. This change in air volume produces a small but accurately measurable pressure change in the air. This equivalence of pressure pulsations in the cuff bladder to volume pulsations of the artery is the essence of oscillometry.

BRIEF DESCRIPTION OF THE DRAWINGS

In order to more fully appreciate the various techniques of the present invention, the following more detailed background information is provided in conjunction with FIGS. 1-5 of the drawings where:

FIG. 1 (corresponding to FIG. 6 in U.S. Pat. No. 3,903,872) diagrammatically illustrates the shapes of successive cuff pressure versus time pulses (cuff pulses) as the measured cuff pressure changes from 90 Torr to 80 Torr to 70 Torr, assuming the patient has a diastolic pressure of 80 Torr;

FIG. 1A diagrammatically illustrates a full series of cuff pulses corresponding to those in FIG. 1 from a cuff pressure of 160 Torr to a cuff pressure of zero;

FIG. 2 diagrammatically illustrates a curve corresponding to arterial or cuff volume (V), that is, the volume of the patient's artery within the cuff (as measured by cuff volume) versus wall pressure ($P_w$) across the artery wall within the cuff and, superimposed on this curve, a curve which is intended to correspond to the actual blood pressure waveform of a patient, the two curves being provided together in order to illustrate the principles of oscillometry, as relied upon in the above-recited patents;

FIGS. 3 and 4 diagrammatically illustrate the cuff curve of FIG. 1 in ways which display techniques for obtaining a given patient's systolic and diastolic blood pressures in accordance with the Link and Link et al patents recited above; and FIG. 5 diagrammatically illustrates a compliance curve for the patient's artery, that is, a curve which displays the ratio $\Delta V/\Delta P$ against the arterial wall pressure $P_w$, where $\Delta V$ is the incremental change in the arterial volume corresponding to a preselected constant change in blood pressure $\Delta P$. This curve is initially determined in order to provide the cuff or arterial volume curve (V/P curve) of FIG. 2 by means of integration, as will be seen.

DESCRIPTION OF THE PREFERRED EMBODIMENTS

Turning first to FIG. 1, this figure diagrammatically illustrates three successive waveforms $10h$, $10i$ and $10j$ which correspond to the change in volume in a pressurized cuff, as described above, at three different cuff pressures, specifically cuff pressures of 90 Torr, 80 Torr and 70 Torr. In actual practice, a greater number of waveforms (hereinafter referred to as cuff pulses) are generated starting at a cuff pressure of 160 Torr and ending at a cuff pressure of zero, as will be seen in FIG. 1A. By generating these waveforms at known cuff pressures, both the diastolic and systolic pressures of a patient can be determined in accordance with the above-recited patents. While this will be explained in more detail below, it is important to note initially that each waveform has what may be referred to as a systolic rise $S_r$ at one end of the waveform, a diastolic decline $D_d$ at the opposite end and a maximum amplitude A.

While the systolic rise $S_r$ is fairly consistent and distinctive from one cuff pulse to another, both the diastolic decline $D_d$ and amplitude A vary from pulse to pulse for reasons to be explained hereinafter. It is because of these variations that the techniques disclosed in the Link and Link et al patents recited above are able to determine the diastolic and systolic pressures. Specifically, as will be seen, when the diastolic pressure of a patient is equal to the cuff pressure, the cuff pulse generated has a diastolic decline which is greater in slope than the diastolic decline of any of the other cuff pulses. Thus, assuming that the diastolic decline has a maximum slope at the cuff pulse $10i$ illustrated in FIG. 1, the patient providing these waveforms would have a diastolic pressure of 80 Torr. At the same time, this patient's systolic pressure can be determined by first finding which of the cuff pulses displays a maximum amplitude A and then, moving up in cuff pressure, finding the cuff pulse having half that amplitude. The cuff pressure responsible for producing this half-amplitude pulse will equal the patient's systolic blood pressure. In order to more fully understand these capabilities, reference is made to FIGS. 2-5 in conjunction with the above-recited Link and Link et al patents.

Turning now to FIG. 2, attention is directed to the curves illustrated there in order to explain why the cuff pulses of FIG. 1 result from changes in cuff pressure. The generally S-shaped curve 12 illustrated is shown with a horizontal/vertical coordinate system where the horizontal axis represents the wall pressure $P_w$ across the artery wall of a given patient, within the confines of the applied cuff, and the vertical axis represents arterial volume V of the artery within the cuff, as measured by the internal volume of the cuff itself. In order to fully understand this V/P curve (hereinafter merely referred to as an arterial or a cuff curve), it is important to keep in kind the definition of $P_w$. The wall pressure $P_w$ of the artery of the patient at any given time is equal to the blood pressure $P_b$ of the patient within the artery at that time less the applied pressure of the cuff $P_c$. Thus:

$$P_w = P_b - P_c \qquad (1)$$

For purposes of the present discussion, it will be assumed that pressure is measured in Torr (mmHg) and that the section of the horizontal axis to the right of the vertical axis represents positive wall pressures while the section of the axis to the left of the vertical axis represents negative wall pressures. As a result, when no pressure is applied to the cuff (e.g. $P_c = 0$), $P_w$ at any given point in time is equal to the blood pressure of the patient at that time. As the cuff is pressurized, $P_w$ decreases (moves to the left along the horizontal axis). When the cuff pressure $P_c$ is equal to the blood pressure $P_b$ at any given point in time, $P_w$ at that time is equal to zero (e.g. at the vertical axis). As the cuff pressure is increased beyond the blood pressure at any point in time, $P_w$ at that time becomes more negative (moves further to the left on the horizontal axis).

With the definitions of the vertical axis V and the horizontal axis $P_w$ in mind, attention is now directed to an interpretation of the generally S-shaped cuff curve 12 within this coordinate system. For the moment, it is being assumed that this curve is characteristic of the particular patient being evaluated. That is, it is being assumed that the patient's artery within the cuff and therefore the cuff itself will change in volume along the S-shaped curve and only along the curve with changes in $P_w$. Hereinafter, with regard to FIG. 3, it will be shown that the arterial curve 12 of a given patient can be generated from his cuff pulses 10 and corresponding cuff pressures $P_c$. Thus, for the time being, it will be assumed that the arterial curve illustrated in FIG. 2 corresponds to that of the given patient.

With the foregoing in mind, the arterial curve of FIG. 2 will now be examined. Let it first be assumed that no pressure is applied to the patient's cuff so that $P_c$ equals zero. As a result, $P_w$ equals the blood pressure $P_b$ of the patient. In this regard, it is important to note that $P_b$ varies with time between the patient's diastolic blood pressure $P_b(D)$ and his systolic blood pressure $P_b(S)$. For purposes of this discussion, let it be assumed that these values are known and that specifically the patient's diastolic blood pressure is 80 Torr and his systolic blood pressure is 120 Torr. Thus, with no pressure in the cuff, $P_w$ oscillates back and forth with time between $P_b(D)$ and $P_b(S)$, that is, between 80 Torr and 120 Torr. This 40 Torr measuring band is illustrated by dotted lines in FIG. 2 at 14 and actually represents the patient's pulse pressure $\Delta P$ which is equal to 40 Torr in this case.

The patient's actual blood pressure waveform 15 is superimposed on the V/$P_w$ coordinate system in FIG. 2 within the pulse pressure band 14. As seen there, this waveform is made up of a series of actual blood pressure pulses 16, each of which corresponds to a single beat of the patient's heart. Note that each pulse starts at a minimum pressure (the diastolic pressure of the patient) and sharply increases along its leading edge which is the systolic rise $S_r$ until it reaches a maximum (the patient's systolic blood pressure), at which time it drops back down along a trailing edge which includes a dichrotic notch and a diastolic decline $D_d$ to the minimum pressure again. At those points in time when the patient's blood pressure is at a minimum (that is, at the diastolic ends of pulses 16), the volume of the patient's artery and therefore the volume of the cuff is fixed by the arterial curve at the value indicated at $V_1(P_w = 80)$. On the other hand, whenever the patient's blood pressure is maximum (at the systolic end of each blood pressure pulse 16), the arterial curve fixes arterial and therefore cuff volume at the slightly higher value indicated at $V_2(P_w = 120)$. Therefore, it should be apparent that for each heart beat, assuming a cuff pressure $P_c$ of zero, the volume V (the cuff volume) moves between the values $V_1$ and $V_2$, thereby generating a series of cuff pulses $10q$ corresponding to those illustrated in FIG. 1 but at a cuff pressure $P_c=0$, as shown in FIG. 1A. Thus, as the patient's blood pressure rises from a minimum to a maximum, the volume of the artery rises from $V_1$ to $V_2$ in a generally corresponding manner and as the patient's blood pressure drops back down to a minimum, the arterial volume falls from $V_2$ to $V_1$ in a generally corresponding manner. Thus, each of the arterial pulses 10 in FIG. 2 has a systolic rise $S_r$ and a diastolic decline $D_d$ corresponding to the systolic rise and diastolic decline of each blood pressure pulse 16.

Having shown how the cuff pulses $10q$ are dependent upon the volume curve at a cuff pressure of zero, we will now describe how the arterial curve causes these arterial pulses to change with applied cuff pressure. Let us assume now a cuff pressure of 50 Torr. Under these conditions, $P_w$ oscillates back and forth between 30 Torr and 70 Torr. The 30 Torr value is determined by subtracting the cuff pressure $P_c$ of 50 Torr from the diastolic blood pressure $P_b(D)$ of 80 Torr and the 70 Torr value is determined by subtracting the same $P_c$ of 50 Torr from the systolic blood pressure $P_b(D)$ of 120 Torr. Thus, the entire 40 Torr band has merely been shifted to the left an amount equal to 50 Torr as indicated by the band 14'. Under these circumstances, $P_w$ oscillates back and forth along a steeper segment of the arterial curve so as to cause the volume of the patient's artery and therefore the volume of the cuff to oscillate between the values $V_3$ and $V_4$. This results in the production of arterial pulses 101 at a $P_c$ of 50 Torr. Note that the amplitude of each cuff pulse 101 is greater than the amplitude of each cuff pulse $10q$. This is because the 40 Torr band 14' at a cuff pressure of 50 Torr is on a steeper part of the volume slope than the band 14 at a cuff pressure of zero. Indeed, as we increase the cuff pressure $P_c$ (which decreases $P_w$) and therefore move the pressure band to the left on the horizontal axis, we first continue to move along steeper sections of the arterial curve and thereafter less steep sections. Therefore, the amplitude A (see FIGS. 1 and 1A) of the corresponding cuff pulses $10q$, 101 and so on will first increase to a maximum and then decrease again. At a cuff pressure $P_c$ of 100, the entire 40 Torr pressure band is shifted to the left so as to uniformly straddle opposite sides of the vertical axis, as indicated at 14''. This results in a corresponding cuff pulse $10g$ having approximately a maximum amplitude ($\Delta V$max in FIG. 2).

Moving still further to the left, at for example, a cuff pressure $P_c$ of 160 Torr, the entire 40 Torr band is moved a substantial distance to the left of the vertical axis, as indicated at 14''' such that the resultant change in volume (amplitude of the corresponding cuff pulse $10a$) is quite small. By increasing the cuff pressure to even a greater amount, the band is moved still further to the left, eventually producing very small changes in volume V. From a physical standpoint, this represents a collapsed artery. In other words, sufficient cuff pressure $P_c$ is being applied over and above the internal blood pressure $P_b$ to cause the wall of the artery to collapse. At the other extreme, that is, when the cuff pressure $P_c$ is zero, there are no external constraints placed on the artery and the latter is free to fluctuate back and forth based on its internal pressure $P_b$ only. Between these extremes, the amplitude A of cuff pulse 10 (e.g. $\Delta V$) will increase to a maximum and then decrease again, as stated. It is this characteristic of the volume curve which is used to determine the patient's systolic pressure in accordance with the previously recited Link et al patents, as will be described with regard to FIGS. 3 and 4.

As previously mentioned, it should be noted that a blood pressure increase causes an arterial volume increase. This arterial volume increase causes a cuff bladder air volume decrease which in turn causes a cuff bladder air-pressure increase. Therefore a blood pressure increase results in a cuff air pressure increase. This is emphasized as follows:

| blood pressure increase | → | arterial volume increase | → | cuff air volume decrease | → | cuff air pressure increase |
|---|---|---|---|---|---|---|
| Thus: | | | | | | |
| | | blood pressure increase | → | cuff air pressure increase | | |

Referring to FIG. 3, the same arterial curve 12 illustrated in FIG. 2 is again shown but with a single superimposed pressure band 14'''' at a cuff pressure $P_c$ of 120 Torr. Assume again that the diastolic pressure of the patient is 80 Torr and his systolic pressure is 120 which means that $P_c$ is equal to the patient's systolic pressure. Under these circumstances, $P_w$ oscillates back and forth within band 14'''' between wall pressures of $-40$ Torr and zero, as shown. This results in a change in arterial volume $\Delta V$ (e.g., the amplitude A of a corresponding cuff pulse) which is approximately equal to one-half of the maximum change in arterial volume (e.g., max cuff pulse amplitude). It may be recalled that a maximum change in volume $\Delta V$ max (and therefore a maximum cuff pulse amplitude Amax) results from a cuff pressure $P_c$ of about 100 Torr (e.g. the pressure band 14'' in FIG. 2). Thus, when the cuff pressure $P_c$ is equal to the patient's systolic blood pressure $P_b(S)$, the amplitude A of the resultant cuff pulse 10 is about one-half of the amplitude of the cuff pulse having a maximum amplitude. Therefore, a patient's systolic blood pressure can be determined by first generating a series of cuff pulses across the cuff pressure spectrum, as in FIG. 1A. From these pulses, the one having maximum amplitude Amax is determined and then the cuff pulse having half that amplitude (at a greater cuff pressure) is found. The cuff pressure $P_c$ used to generate that pulse corresponds to the patient's systolic pressure. In other words, by evaluating the amplitudes of the various cuff pulses, the one corresponding to the band 14'''' illustrated in FIG. 3 can be found. Once that pulse is found, its associated cuff pressure is assumed to be equal to the patient's systolic pressure. This is discussed in more detail in Link et al U.S. Pat. Nos. 4,009,709 and 4,074,711 and means are provided in these latter patents for electronically making these evaluations.

Returning to FIG. 2, it should be noted that the actual blood pressure waveform 15 is shown having a uniform repetition rate, for example 60 pulses/minute, and that each blood pressure pulse 16 making up this waveform is identical to the next one. Both of these aspects of the waveform are assumed for purposes herein. Moreover, each pulse has its own systolic rise $S_r$ and diastolic decline $D_d$, as mentioned heretofore. It should also be noted that the arterial curve 12 dictates the relationship between V and $P_w$ at each and every point on the waveform 15 of individual blood pressure pulse 16, not merely at the extreme diastolic and systolic end points of each pulse. Thus, one could measure the change in volume $\Delta V$ at two different cuff pressures along the diastolic decline only. In this case, the measuring band (e.g. the pressure difference between the two measuring points) is substantially narrower than band 14. As best illustrated in FIG. 4, $\Delta V_1'$ is determined for a cuff pressure $P_c$ of zero using the pressure band 18 which encompasses a small part of the diastolic decline of each blood pressure pulse 16. $\Delta V_2'$ is determined for a cuff pressure of $P_c$ of 50 Torr by shifting the band to 18' and, $\Delta V_3'$ is determined for a cuff pressure $P_c$ of 80 Torr (e.g. the patient's diastolic blood pressure) by shifting the band to 18''. Note that $\Delta V$ is maximum when the cuff pressure $P_c$ is equal to the patient's diastolic blood pressure. Therefore, by determining the change in volume $\Delta V$ at the end of the diastolic slope of the patient's actual blood pressure waveform for each and every cuff pressure, the one cuff pressure producing a maximum change will correspond to the patient's diastolic blood pressure. The lowest pressure part of the diastolic decline $D_d$ forming part of each pulse 16 is particularly suitable for this purpose since it can be readily located during each cycle of the waveform. This is because it immediately precedes the systolic rise $S_r$ which is readily distinguishable each time it appears. This procedure is described in more detail in the previously recited Link U.S. Pat. No. 3,903,872 along with means for carrying out this procedure electronically.

The foregoing discussions for obtaining a given patient's systolic and diastolic blood pressures have assumed that the patient's arterial curve corresponded to the one illustrated in FIGS. 2, 3 and 4. While this assumption is reasonably valid, it is possible to determine the patient's own volume curve using the principles associated with FIG. 4. Specifically, using the narrower bands 18, 18' and so on as measuring bands, the change in volume $\Delta V$ (e.g., the change in cuff volume) resulting from different cuff pressures $P_c$ is plotted, as shown in FIG. 5. Thus at a cuff pressure $P_c$ of zero, there is a relatively small change in volume $\Delta V$, as evidenced by the small $\Delta V_1'$ in FIG. 4. As the cuff pressure $P_c$ increases, the change in volume $\Delta V$ continues to increase to a maximum ($\Delta V_3'$ in FIG. 4) and then decreases. In mathematical terms, this curve represents incremental changes in volume with incremental changes in pressure or $dV/dP$ (FIG. 5). By integrating this curve we obtain the cuff curve or the V/P curve of FIGS. 2-4.

Having discussed FIGS. 1-5 in regards to the prior art techniques for obtaining diastolic and systolic blood pressures for a given patient in accordance with the techniques described in the above-recited Link and Link et al patents, attention is now directed to the present invention, as discussed briefly above, in conjunction with remaining FIGS. 6-8 where:

FIG. 6 graphically displays the peak to peak amplitude (A) of various cuff pulses of FIG. 1A against cuff pressure;

FIG. 7 graphically illustrates a way of obtaining a given patient's systolic blood pressure in accordance with the present invention; and FIG. 8 schematically illustrates an arrangement for obtaining the systolic blood pressure in accordance with the method illustrated in FIG. 7.

Turning now to FIGS. 6-8, attention is directed to the present invention which is to provide a new technique for determining an individual patient's systolic blood pressure. It may be recalled from previous discussions relating to FIG. 3 and Link et al U.S. Pat. Nos. 4,009,709 and 4,074,711, a prior art technique for determining a patient's systolic blood pressure uses his cuff pulses to this end. Specifically, the cuff pulse having the maximum peak to peak value is found and this value is halved. Thereafter, the particular cuff pulse having this same halved peak to peak value at a greater cuff pressure is found. This latter cuff pressure corresponds to the patient's systolic blood pressure. Using for example the cuff pulses illustrated in FIG. 1A, it should be quite apparent that the pulse corresponding to a cuff pressure of 90 Torr (Pulse 10h) has a maximum peak to peak value of 2.9 Torr. Dividing this value by two results in a value of approximately 1.5 Torr. The cuff pulse having a peak to peak amplitude of 1.5 Torr and a cuff pressure greater than 90 lies approximately between the cuff pulses 10d and 10e illustrated in FIG. 1A, that is, the pulse having a cuff pressure between 120 and 130 Torr or about 125 Torr.

In accordance with the present invention, a different approach is taken. This approach uses the A versus $P_c$ curve 40 of FIG. 6 using the cuff pulses of FIG. 1A, as redrawn in FIG. 7 as curve 50. As discussed in copending Link Patent Application Ser. No. 622,080 filed June 19, 1984, entitled A TECHNIQUE FOR GENERATING AN ARTERIAL CURVE ASSOCIATED WITH AN INDIVIDUAL'S BLOOD PRESSURE, the curve 40 of FIG. 6 can be used in conjunction with the previously measured diastolic and systolic blood pressures to generate the individual's arterial V/P curve and dV/dP curves. (Both the diastolic and systolic blood pressures of the patient can be measured in various known ways.) In the present case, it is assumed that the diastolic pressure is known from prior techniques, for example Link U.S. Pat. No. 3,903,872 but that the systolic pressure is not known. For this reason, it is not possible to generate an arterial V/P curve the way in which it was generated in the last mentioned copending Link application. However, it is possible to generate the patient's arterial V/P curve in the manner described previously in conjunction with FIGS. 2-5 and the U.S. Pat. No. '872 patent and this technique does not require knowing the patient's systolic pressure. Therefore, once we have the patient's arterial V/P curve, we can work backwards from this curve to generate a corresponding $A/P_c$ (where A is the peak to peak amplitude of the cuff pulses of FIG. 1A and $P_c$ is the cuff pressure) curve from an assumed systolic pressure since we know the diastolic pressure. Therefore, if we, for example, assume a systolic pressure of 135 Torr, a corresponding $A/P_c$ curve 52 can be generated, as indicated in FIG. 7. A similar curve 54 can be generated for an assumed systolic pressure of 115 Torr. Note that neither of these two latter curves correspond exactly to the $A/P_c$ curve 50 corresponding to the one in FIG. 6. However, one which is generated on an assumed systolic blood pressure of 125 Torr will closely correspond to the curve corresponding to the one in FIG. 6. Therefore, this latter assumed value, that is, a value of 125 Torr most closely corresponds to the patient's actual systolic pressure.

Another very similar procedure to closely estimate the systolic pressure is actually the inverse of the above. To understand this, we briefly review the method described above using somewhat different phraseology.

Two experimental curves are first obtained from a patient using a blood pressure apparatus such as described in the Link U.S. Pat. Nos. 3,903,872, 4,009,709 and 4,074,711. These experimental curves are firstly the arterial volume/pressure (V/P) curve and secondly the peak to peak cuff pulse amplitude versus cuff pressure (A/P$_c$) curve. Additionally the diastolic pressure (P$_d$) of the patient is determined using means described for instance in the Link U.S. Pat. No. 3,903,872. Now the two curves described above are not independent of one another, for if the patients diastolic and systolic pressures are known; either one of the two above curves can be derived from the other, that is for known P$_d$ and P$_s$ the V/P curve can be used to derive the A/P$_c$ curve or the A/P$_c$ curve can be used to derive the V/P curve. If both curves are known and P$_d$ is known, then the above procedure can be used to accurately estimate P$_s$, for only a correct assumed value of P$_s$ can be used together with P$_d$ to correctly derive either one of the known experimental curves from the other. Therefore, although the method described above derives the A/P$_c$ curve from the V/P curve given a measured P$_d$ and an assumed P$_s$, obviously the inverse procedure could be used in which the V/P curve is derived from the A/P$_c$ curve given a measured P$_d$ and an assumed P$_s$. Both of the above methods, although the inverse of each other, can be used to accurately estimate the systolic pressure P$_s$.

In FIG. 8, means 24 is provided for receiving peak to peak information from transducer 14 which measures cuff pulses from a cuff and pressure changing means 25 in the same manner as pulses 10a–10q of FIG. 1A are obtained. At the same time, means 24 receives the patient's diastolic blood pressure and his cuff (V/P) curve from, means described in, for example, the Link U.S. Pat. No. 3,903,872. Also at the same time, different assumed systolic blood pressures may be fed into the means 24 which has readily providable circuitry to act on all of this information in order to carry out the procedure just discussed and produce at its output the value which best approximates the patient's actual systolic blood pressure.

What is claimed is:

1. A method of determining the systolic pressure of a given mammal, comprising the steps of:
   (a) determining the diastolic pressure of said mammal;
   (b) establishing an arterial curve characteristic of said mammal in a way which does not require the systolic pressure;
   (c) placing a blood pressure cuff around a particular artery of said mammal;
   (d) pressurizing the cuff at a number of different pressure levels from zero pressure to a pressure at least equal to the mammal's systolic pressure and generating cuff pulses having peak to peak amplitude values corresponding to and dependent on said different pressure levels;
   (e) graphically providing a reference curve of said peak to peak amplitude values against said pressure levels;
   (f) using said arterial curve, said diastolic pressure and an assumed systolic pressure, obtaining peak to peak amplitude values at different cuff pressures from this information and graphically providing a comparison curve of these latter peak to peak amplitude values against said different cuff pressures;
   (g) comparing said reference curve with said comparison curve, whereby if they are similar, then the assumed systolic pressure is approximately equal to the given mammal's actual systolic pressure; and
   (h) repeating steps (f) and (g) for one or more different assumed systolic pressures if said first-mentioned comparison curve is different than said reference curve until a comparison curve is established which corresponds to said reference curve.

2. An apparatus for determining the systolic pressure of a given mammal, comprising:
   (a) means for determining the diastolic pressure of said mammal;
   (b) means for establishing an arterial curve characteristic of said mammal in a way which does not require the systolic pressure;
   (c) a blood pressure cuff for placement around a particular artery of said mammal;
   (d) means cooperating with said cuff for pressurizing the latter at a number of different pressure levels from zero pressure to a pressure at least equal to the mammal's systolic pressure and for generating cuff pulses having peak to peak amplitude values corresponding to and dependent on said different pressure levels;
   (e) means for graphically providing a reference curve of said peak to peak amplitude values against said pressure levels;
   (f) means responsive to said arterial curve, said diastolic pressure and an assumed systolic pressure for obtaining peak to peak amplitude values at different cuff pressures from this information and graphically providing a comparison curve of these latter peak to peak amplitude values against said different cuff pressures;
   (g) means for comparing said reference curve with said comparison curve, whereby if they are similar, then the assumed systolic pressure is approximately equal to the given mammal's actual systolic pressure; and
   (h) means for repeating the functions carried out by the responsive means and the comparing means for one or more different assumed systolic pressures if said first-mentioned comparison curve is different than said reference curve until a comparison curve is established which corresponds to said reference curve.

3. A method of determining the systolic pressure of a given mammal, comprising the steps of:
   (a) determining the diastolic pressure of said mammal;
   (b) establishing an arterial reference curve characteristic of said mammal in a way which does not require the systolic pressure;
   (c) placing a blood pressure cuff around a particular artery of said mammal;
   (d) pressurizing the cuff at a number of different pressure levels from zero pressure to a pressure at least equal to the mammal's systolic pressure, generating cuff pulses having peak to peak amplitude values corresponding to and dependent on said different pressure levels and establishing an amplitude curve from these values;
   (e) using said amplitude curve, said diastolic pressure and an assumed systolic pressure, obtaining from this information and graphically providing an arterial comparison curve;
   (f) comparing said arterial reference curve with said arterial comparison curve, whereby if they are similar, then the assumed systolic pressure is approximately equal to the given mammal's actual systolic pressure; and
   (g) repeating steps (e) and (f) for one or more different assumed systolic pressures if said first-mentioned comparison curve is different than said reference curve until a comparison curve is established which corresponds to said reference curve.

4. An apparatus for determining the systolic pressure of a given mammal, comprising:
   (a) means for determining the diastolic pressure of said mammal;
   (b) means for establishing an arterial reference curve characteristic of said mammal in a way which does not require the systolic pressure;
   (c) a blood pressure cuff for placement around a particular artery of said mammal;
   (d) means cooperating with said cuff for pressurizing the latter at a number of different pressure levels from zero pressure to a pressure at least equal to the mammal's systolic pressure, for generating cuff pulses having peak to peak amplitude values corresponding to and dependent on said different pressure levels and for establishing an amplitude curve from these values;
   (e) means responsive to said amplitude curve, said diastolic pressure and an assumed systolic pressure for obtaining from this information and graphically providing an arterial comparison curve;
   (f) means for comparing said arterial reference curve with said arterial comparison curve, whereby if they are similar, then the assumed systolic pressure is approximately equal to the given mammal's actual systolic pressure; and
   (g) means for repeating the functions carried out by the responsive means and the comparing means for one or more different assumed systolic pressures if said first-mentioned comparison curve is different than said reference curve until a comparison curve is established which corresponds to said reference curve.

5. A method of determining the systolic pressure of a given mammal, comprising the steps of:
   (a) determining the diastolic pressure of said mammal;
   (b) establishing an arterial curve characteristic of said mammal in a way which does not require the systolic pressure;
   (c) placing a blood pressure cuff type member adjacent a particular artery of said mammal;
   (d) pressurizing the cuff-type member at a number of different pressure levels from zero pressure to a pressure at least equal to the mammal's systolic pressure and generating cuff pulses having peak to peak amplitude values corresponding to and dependent on said different pressure levels;
   (e) providing a reference curve of said peak to peak amplitude values against said pressure levels;
   (f) using said arterial curve, said diastolic pressure and an assumed systolic pressure, obtaining peak to peak amplitude values at different cuff pressures from this information and providing a comparison curve of these latter peak to peak amplitude values against said different cuff pressures;
   (g) comparing said reference curve with said comparison curve, whereby if they are similar, then the assumed systolic pressure is approximately equal to the given mammal's actual systolic pressure; and
   (h) repeating steps (f) and (g) for one or more different assumed systolic pressures if said first-mentioned comparison curve is different than said reference curve until a comparison curve is established which corresponds to said reference curve.

6. An apparatus for determining the systolic pressure of a given mammal, comprising:
   (a) means for determining the diastolic pressure of said mammal;
   (b) means for establishing an arterial curve characteristic of said mammal in a way which does not require the systolic pressure;
   (c) blood pressure cuff means for placement adjacent a particular artery of said mammal;
   (d) means cooperating with said cuff means for pressurizing the latter at a number of different pressure levels from zero pressure to a pressure at least equal to the mammal's systolic pressure and for generating cuff pulses having peak to peak amplitude values corresponding to and dependent on said different pressure levels;
   (e) means for providing a reference curve of said peak to peak amplitude values against said pressure levels;
   (f) means responsive to said arterial curve, said diastolic pressure and an assumed systolic pressure for obtaining peak to peak amplitude values at different cuff pressures from this information and providing a comparison curve of these latter peak to peak amplitude values against said different cuff pressures;
   (g) means for comparing said reference curve with said comparison curve, whereby if they are similar, then the assumed systolic pressure is approximately equal to the given mammal's actual systolic pressure; and
   (h) means for repeating the functions carried out by the responsive means and the comparing means for one or more different assumed systolic pressures if said first-mentioned comparison curve is different than said reference curve until a comparison curve is established which corresponds to said reference curve.

7. A method of determining the systolic pressure of a given mammal, comprising the steps of:
   (a) determining the diastolic pressure of said mammal;
   (b) establishing an arterial reference curve characteristic of said mammal in a way which does not require the systolic pressure;
   (c) placing a blood pressure cuff type member adjacent a particular artery of said mammal;
   (d) pressurizing the cuff-type member at a number of different pressure levels from zero pressure to a pressure at least equal to the mammal's systolic pressure, generating cuff pulses having peak to peak amplitude values corresponding to and dependent on said different pressure levels and establishing an amplitude curve from these values;
   (e) using said amplitude curve, said diastolic pressure and an assumed systolic pressure, obtaining from this information an arterial comparison curve;
   (f) comparing said arterial reference curve with said arterial comparison curve, whereby if they are similar, then the assumed systolic pressure is approximately equal to the given mammal's actual systolic pressure; and
   (g) repeating steps (e) and (f) for one or more different assumed systolic pressures if said first-mentioned comparison curve is different than said reference curve until a comparison curve is established which corresponds to said reference curve.

8. An apparatus for determining the systolic pressure of a given mammal, comprising:
   (a) means for determining the diastolic pressure of said mammal;

(b) means for establishing an arterial reference curve characteristic of said mammal in a way which does not require the systolic pressure;

(c) blood pressure cuff means for placement adjacent a particular artery of said mammal;

(d) means cooperating with said cuff means for pressurizing the latter at a number of different pressure levels from zero pressure to a pressure at least equal to the mammal's systolic pressure, for generating cuff pulses having peak to peak amplitude values corresponding to and dependent on said different pressure levels, and for establishing an amplitude curve from these values;

(e) means responsive to said amplitude curve, said diastolic pressure and an assumed systolic pressure for obtaining from this information an arterial comparison curve;

(f) means for comparing said arterial reference curve with said arterial comparison curve, whereby if they are similar, then the assumed systolic pressure is approximately equal to the given mammal's actual systolic pressure; and (g) means for repeating the functions carried out by the responsive means and the comparing means for one or more different assumed systolic pressures if said first-mentioned comparison curve is different than said reference curve until a comparison curve is established which corresponds to said reference curve.

* * * * *